(12) United States Patent
Matsumoto et al.

(10) Patent No.: US 8,541,215 B2
(45) Date of Patent: Sep. 24, 2013

(54) MICROORGANISMS, SELENIUM ACID COMPOUND-REDUCING AGENT, METHOD FOR REDUCING AND METHOD FOR REMOVING SELENIUM ACID COMPOUND, AND PROCESS FOR PRODUCING METALLIC SELENIUM

(75) Inventors: Mitsufumi Matsumoto, Kitakyusyu (JP); Yasuhiko Nishimura, Kitakyusyu (JP)

(73) Assignee: Electric Power Development Co., Ltd., Tokyo (JP)

( * ) Notice: Subject to any disclaimer, the term of this patent is extended or adjusted under 35 U.S.C. 154(b) by 213 days.

(21) Appl. No.: 12/737,166

(22) PCT Filed: Jun. 17, 2009

(86) PCT No.: PCT/JP2009/061042
§ 371 (c)(1),
(2), (4) Date: Dec. 13, 2010

(87) PCT Pub. No.: WO2009/154234
PCT Pub. Date: Dec. 23, 2009

(65) Prior Publication Data
US 2011/0207193 A1    Aug. 25, 2011

(30) Foreign Application Priority Data

Jun. 18, 2008    (JP) .................. 2008-159224

(51) Int. Cl.
| *C12P 3/00* | (2006.01) |
| *C12N 9/00* | (2006.01) |
| *C12N 1/12* | (2006.01) |
| *C02F 3/34* | (2006.01) |
| *C07H 21/04* | (2006.01) |

(52) U.S. Cl.
USPC ........ 435/168; 435/183; 435/252.1; 435/262; 536/23.2

(58) Field of Classification Search
None
See application file for complete search history.

(56) References Cited

FOREIGN PATENT DOCUMENTS

| JP | 9-224656 | 9/1997 |
| JP | 9-248595 | 9/1997 |
| JP | 10-84948 | 4/1998 |
| JP | 10-165197 | 6/1998 |
| JP | 10-309190 | 11/1998 |
| JP | 2000-253869 | 9/2000 |
| JP | 2005-341817 | 12/2005 |
| JP | 2007-289912 | 11/2007 |
| JP | 2008-12461 | 1/2008 |

OTHER PUBLICATIONS

Hunter et al. Curr Microbiol. Apr. 2006;52(4):305-9. Epub Mar. 18, 2006.*
Zhang et al. Bioresour Technol. Mar. 2008;99(5):1267-73. Epub May 18, 2007.*
Oremland, R. S. et al., Simultaneous reduction of nitrate and selenate by cell suspensions of selenium-respiring bacteria, Appl. Environ Microbiol, 1999, vol. 65, No. 10, pp. 4385-4392.
M. E. Losi et al., "Reduction of Selenium Oxyanions by Enterobacter cloacae SLD1a-1: Isolation and Growth of the Bacterium and Its Expulsion of Selenium Particles," Applied and Environmental Microbiology, Aug. 1997, vol. 63, No. 8, pp. 3079-3084.
S. F. Altschul et al., "Gapped BLAST and PSI-BLAST: a new generation of protein database search programs," Nucleic Acids Research, 1997, vol. 25, No. 17, pp. 3389-3402.
"Validation of the Publication of New Names and New Combinations Previously Effectively Published Outside the IJSB," List No. 44, Int. j. Syst. Bacteriol Jan. 1993, vol. 43, No. 1, pp. 188-189.
Y. Kodama et al., "*Sulfurospirillum cavolei* sp. nov., a facultatively anaerobic sulfur-reducing bacterium isolated from an underground crude oil storage cavity," Int. j. Syst. Evol. Microbiol., 2007, 57, pp. 827-831.
M. Kashiwa et al., "Removal of soluble selenium by a selenate-reducing bacterium *Bacillus* sp. SF-1," Biofactors, 14 (2001), pp. 261-265.
Oremland, R. S. et al., Structural and spectral features of selenium nanospheres produced by Se-respiring bacteria, Appl. Environ Microbiol, 2004, vol. 70, No. 1, pp. 52-60.
Remland, R. S. et al., Simultaneous reduction of nitrate and selenate by cell suspensions of selenium-respiring bacteria, Appl. Environ Microbiol, 1999, vol. 65, No. 10, pp. 4385-4392.
Hunter, W. J. et al., Identification and characterization of an *Aeromonas salmonicida* (syn *Haemophilus piscium*) strain that reduces selenite to elemental red selenium, Curr icrobiol, 2006, vol. 52, No. 4, pp. 305-309.

* cited by examiner

*Primary Examiner* — Christian Fronda
(74) *Attorney, Agent, or Firm* — Kenyon & Kenyon LLP

(57) ABSTRACT

Disclosed are novel microorganisms having an excellent ability to reduce selenium acid compounds, a selenium acid compound-reducing agent comprising such microorganism(s) as an active ingredient, a method for reducing and a method for removing a selenium acid compound with use of such microorganism(s), and a process for producing metallic selenium. The microorganisms of the present invention are *Aeromonas* sp. strain JPCC SEP JP-1, *Klebsiella* sp. strain JPCC SEP JP-2, and *Sulfurospirillum* sp. strain JPCCY SEP-3. Also disclosed are a method for reducing a selenium acid compound comprising the step of co-culturing these microorganisms under the presence of a selenium acid compound, and a process for producing metallic selenium comprising the steps of: co-culturing these microorganisms under the presence of a selenium acid compound; and separating the thus produced culture product.

6 Claims, 5 Drawing Sheets

MICROORGANISMS, SELENIUM ACID COMPOUND-REDUCING AGENT, METHOD FOR REDUCING AND METHOD FOR REMOVING SELENIUM ACID COMPOUND, AND PROCESS FOR PRODUCING METALLIC SELENIUM

SEQUENCE LISTING

The instant application contains a Sequence Listing which has been submitted in ASCII text via EFS-Web and is hereby incorporated by reference in its entirety. Said ASCII copy, created on Apr. 29, 2011, is named SequenceListing.txt and is 6,665 bytes in size.

TECHNICAL FIELD

The present invention relates to novel microorganisms, a selenium acid compound-reducing agent comprising such microorganism(s) as an active ingredient, a method for reducing and a method for removing a selenium acid compound with use of such microorganism(s), and a process for producing metallic selenium.

Priority is claimed on Japanese Patent Application No. 2008-159224, filed Jun. 18, 2008, the content of which is incorporated herein by reference.

BACKGROUND ART

Selenium is a valuable element of high use in the industrial world since it is known to be useful as a semiconductor material or a photosensitive material and it can also be used as a glass colorant or decolorant.

On the other hand, it is known that selenium becomes toxic if taken in excess, although a trace amount of selenium is an essential element for a human body. Therefore, selenium is an item to be assessed for the environmental standard in order to prevent water pollution and soil pollution.

In such a situation, it may be possible that waste water from factories in the above-mentioned industrial world is contaminated by selenium. Moreover, because a small amount of selenium is also contained in coal, it may also be possible that waste water from thermoelectric power plants is contaminated by selenium. Therefore, the removal of selenium from such waste water has been an important task.

Selenium being a problem in waste water from factories is selenic acid ($H_2SeO_4$) which is a hexavalent selenium compound, or a salt thereof, and selenious acid ($H_2SeO_3$) which is a tetravalent selenium compound, or a salt thereof. It is considered that most parts of these selenium acid compounds are present in a form of selenate ion ($SeO_4^{2-}$) and very small parts thereof are present in a form of selenite ion ($SeO_3^{2-}$) in an aqueous solution such as waste water from factories. These selenium acid compounds become zero-valent metallic selenium when reduced.

Incidentally, some microorganisms in the natural world are known to intake these selenium oxyanions into their bodies to carry out a reduction treatment. Specifically, specific kinds of microorganisms, when grown under the presence of selenium oxyanions and a nutrition source, do intake these anions into their bodies and reduce selenate ions into selenite ions as they grow, and furthermore reduce the selenite ions into particulate metallic selenium (for example, refer to Patent Document 1 and Non Patent Document 1). This phenomenon is known as biomineralization, and it is possible with use of this phenomenon to remove selenium oxyanions from a solution while particulating them.

In addition, some extracellular polymeric substances such as polysaccharides, lipids, and vacuoles residing on cell surfaces of microorganisms are able to adsorb selenium oxyanions. This phenomenon is known as bioadsorption. It is said to be possible also with this phenomenon to remove selenium oxyanions from a solution.

The method for removing selenium acid compounds from waste water with the aid of microorganisms in this way can be said to be an excellent method as it imposes less load to the environment.

PRIOR ART DOCUMENTS

Patent Documents

Patent Document 1: Japanese Unexamined Patent Application, First Publication No. H9-248595

Non Patent Documents

Non Patent Document 1: Applied and Environmental Microbiology, Vol. 63, No. 8, p 3079-3084.

DISCLOSURE OF INVENTION

Problems to be Solved by the Invention

However, in the removal of selenium oxyanions by means of conventional biomineralization such as those of Patent Document 1 and Non Patent Document 1, the present state is that microorganisms having much higher removal ability are needed. A slow reduction rate to reduce selenite ions into metallic selenium can be considered to be one of the main reasons. For example, microorganisms belonging to the genus *Bacillus* disclosed in Patent Document 1 are deemed to have the highest selenium oxyanion removal rate, among microorganisms reported so far. However, even with use of these microorganisms, it still takes about 100 hours to completely reduce 1 mM selenate ion into metallic selenium.

Moreover, regarding the removal of selenium oxyanions by means of bioadsorption, the present state is that no practical method has been established yet.

The present invention takes such situations into consideration with an object of providing novel microorganisms having excellent ability to reduce selenium acid compounds, a selenium acid compound-reducing agent comprising such microorganism(s) as an active ingredient, a method for reducing and a method for removing a selenium acid compound with use of such microorganism(s), and a process for producing metallic selenium.

Means for Solving the Problems

In order to solve the above object, the inventors of the present invention have conducted intensive studies. This has led to the completion of the following inventive aspects (1) to (16).

(1) A method for reducing a selenium acid compound, comprising the step of co-culturing a microorganism belonging to a species to which a strain JPCC SEP JP-1 of the genus *Aeromonas* belongs, a microorganism belonging to a species to which a strain JPCC SEP JP-2 of the genus *Klebsiella* belongs, and a microorganism belonging to a species to which a strain JPCCY SEP-3 of the genus *Sulfurospirillum* belongs, under the presence of a selenium acid compound.

(2) A method for removing a selenium acid compound, comprising the step of co-culturing a microorganism belonging to a species to which a strain JPCC SEP JP-1 of the genus *Aeromonas* belongs, a microorganism belonging to a species to which a strain JPCC SEP JP-2 of the genus *Klebsiella* belongs, and a microorganism belonging to a species to which a strain JPCCY SEP-3 of the genus *Sulfurospirillum* belongs, under the presence of a selenium acid compound.

(3) A process for producing metallic selenium, comprising the steps of: co-culturing a microorganism belonging to a species to which a strain JPCC SEP JP-1 of the genus *Aeromonas* belongs, a microorganism belonging to a species to which a strain JPCC SEP JP-2 of the genus *Klebsiella* belongs, and a microorganism belonging to a species to which a strain JPCCY SEP-3 of the genus *Sulfurospirillum* belongs, under the presence of a selenium acid compound; and separating the thus produced culture product.

(4) A microorganism belonging to a species to which a strain JPCC SEP JP-1 of the genus *Aeromonas* belongs.

(5) A microorganism belonging to the genus *Aeromonas*, which has an ability to reduce a selenium acid compound, and the 16S rDNA sequence of which consists of a nucleotide sequence having a 96% or higher homology with the nucleotide sequence represented by SEQ ID NO: 1.

(6) A strain JPCC SEP JP-1 of the genus *Aeromonas*.

(7) A microorganism belonging to a species to which a strain JPCC SEP JP-2 of the genus *Klebsiella* belongs.

(8) A microorganism belonging to the genus *Klebsiella*, which has an ability to reduce a selenium acid compound, and the 16S rDNA sequence of which consists of a nucleotide sequence having a 96% or higher homology with the nucleotide sequence represented by SEQ ID NO: 2.

(9) A strain JPCC SEP JP-2 of the genus *Klebsiella*.

(10) A microorganism belonging to a species to which a strain JPCCY SEP-3 of the genus *Sulfurospirillum* belongs.

(11) A microorganism belonging to the genus *Sulfurospirillum*, which has an ability to reduce a selenium acid compound, and the 16S rDNA sequence of which consists of a nucleotide sequence having a 96% or higher homology with the nucleotide sequence represented by SEQ ID NO: 3.

(12) A strain JPCCY SEP-3 of the genus *Sulfurospirillum*.

(13) A selenium acid compound-reducing agent, comprising the microorganism according to any one of (4) to (12) as an active ingredient.

(14) A method for reducing a selenium acid compound, comprising the step of culturing the microorganism according to any one of (4) to (12) under the presence of a selenium acid compound.

(15) A method for removing a selenium acid compound, comprising the step of culturing the microorganism according to any one of (4) to (12) under the presence of a selenium acid compound.

(16) A process for producing metallic selenium, comprising the steps of: culturing the microorganism according to any one of (4) to (12) under the presence of a selenium acid compound; and separating the thus produced culture product.

Effects of the Invention

According to the present invention, selenium acid compounds in waste water or such an environment can be quickly removed.

BEST MODE FOR CARRYING OUT THE INVENTION

Figure 1:
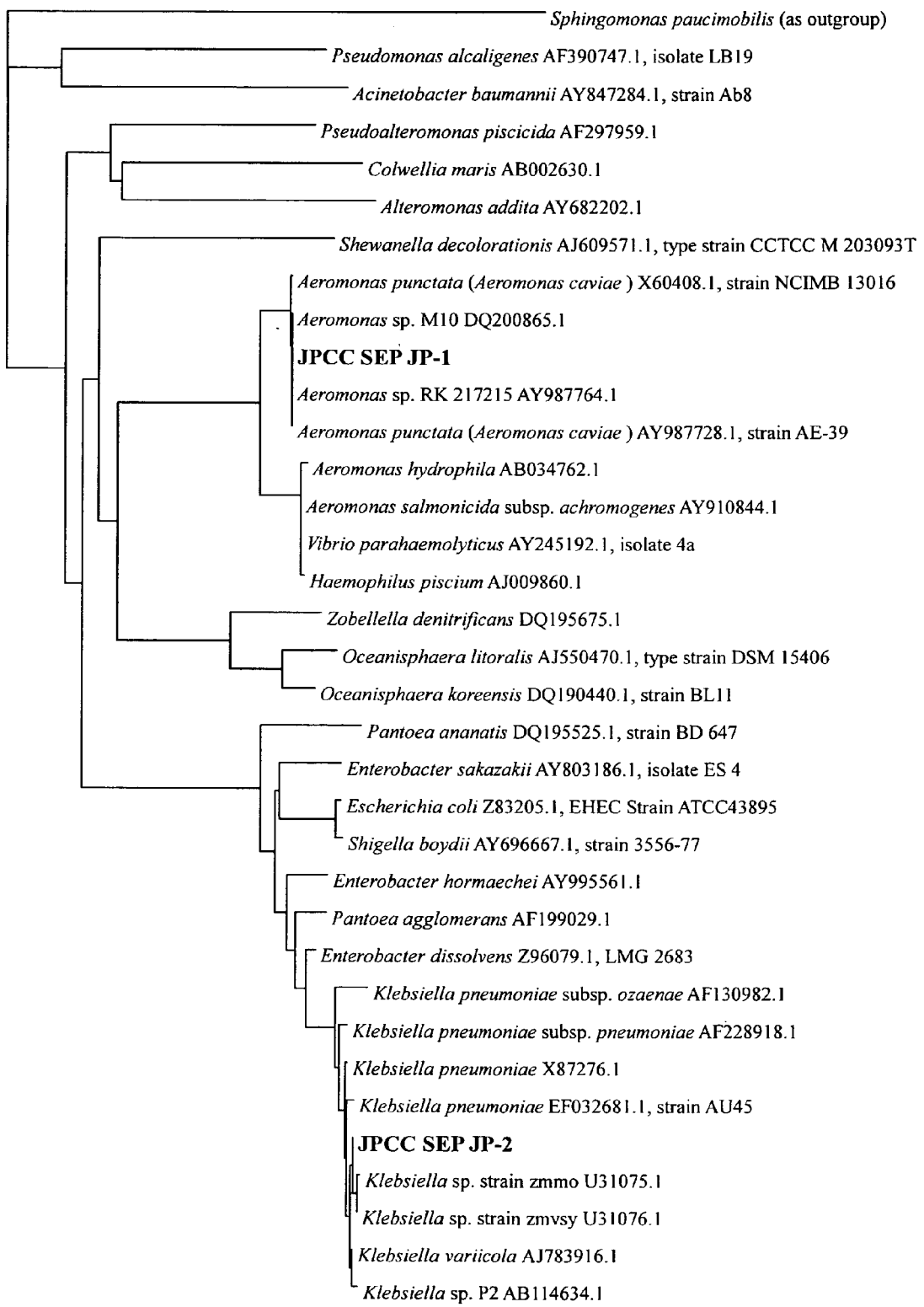
FIG. 1 is a molecular phylogenetic tree showing the results of the molecular phylogenetic analyses on the 16S rDNAs of JPCC SEP JP-1 and JPCC SEP JP-2.

Hereunder is a detailed description of the present invention. Hereinbelow, the "strain JPCC SEP JP-1 of the genus *Aeromonas*" may be abbreviated as the term "*Aeromonas* sp. strain JPCC SEP JP-1" or the term "JPCC SEP JP-1". In addition, the "strain JPCC SEP JP-2 of the genus *Klebsiella*" may be abbreviated as the term "*Klebsiella* sp. strain JPCC SEP JP-2" or the term "JPCC SEP JP-2". Moreover, the "strain JPCCY SEP-3 of the genus *Sulfurospirillum*" may be abbreviated as the term "*Sulfurospirillum* sp. strain JPCCY SEP-3" or the term "JPCCY SEP-3".

In the present invention, the term selenium acid compound refers to selenic acid, selenious acid, salts thereof, and ions thereof.

Acquisition of JPCC SEP JP-1, JPCC SEP JP-2, and JPCCY SEP-3

JPCC SEP JP-1, JPCC SEP JP-2, and JPCCY SEP-3 of the present invention are found in soil of a mangrove forest in Amami Island, and can be acquired through culture and purification of samples collected from this soil.

The culture and purification of samples are conducted by the following manner, for example. The samples are cultured with use of a sterilized medium, preferably a liquid medium, under the presence of a selenium acid compound. A medium in which the growth of JPCC SEP JP-1, JPCC SEP JP-2, or JPCCY SEP-3 can be confirmed is selected and further subjected to a repetition of culture. By so doing, these microorganisms can be acquired. The growth of JPCC SEP JP-1, JPCC SEP JP-2, and JPCCY SEP-3 can be confirmed by checking the presence or absence of red coloration of the medium. This red coloration is caused by metallic selenium within the bodies of these microorganisms. Moreover, JPCC SEP JP-1, JPCC SEP JP-2, and JPCCY SEP-3 are able to be distinguished from other microorganisms by checking the shapes and the selenium removing activities of these microorganisms. JPCC SEP JP-1, JPCC SEP JP-2, and JPCCY SEP-3 themselves can also be distinguished from each other by checking their morphological properties, physiological properties, and other properties, which will be described later.

The medium for use in the culture of JPCC SEP JP-1, JPCC SEP JP-2, and JPCCY SEP-3 is not specifically limited as long as it contains such as a carbon source, a nitrogen source, inorganic salts, trace elements, yeast extract, and other ingredients, which are necessary for the growth of these microorganisms.

The carbon source can be exemplified by alcohols such as methanol and ethanol and organic acids such as acetic acid and lactic acid. Of these, preferred are lactic acid and ethanol, and particularly preferred is lactic acid.

The nitrogen source can be exemplified by nitrates and ammonium salts.

The inorganic salts can be exemplified by potassium or sodium salts of phosphoric acid, sodium chloride, calcium chloride, and magnesium chloride.

The trace elements can be exemplified by iron, cobalt, copper, zinc, boron, nickel, and molybdenum.

Of these, a preferred medium can be exemplified by the liquid ME medium having the following composition.

ME medium composition; 0.6 g of lactic acid, 0.5 g of potassium dihydrogen phosphate, 0.2 g of ammonium chloride, 0.05 g of cysteine, 0.2 g of yeast extract, 1 L of distilled water, and 4 ml of mineral liquid.

The composition of the mineral liquid is as follows.

Mineral liquid composition; 1.8 g of nitrilotriacetic acid, 2.5 g of magnesium chloride hexahydrate, 0.6 g of manganese (II) chloride tetrahydrate, 1.0 g of sodium chloride, 0.136 g of iron (II) chloride tetrahydrate, 0.1 g of cobalt (II) chloride hexahydrate, 0.13 g of calcium chloride dihydrate, 0.0146 g of copper (II) sulfate pentahydrate, 0.01 g of zinc chloride, 0.01 g of boric acid ($H_3BO_3$), 0.01 g of nickel (II) chloride hexahydrate, 0.01 g of sodium molybdate (VI) dihydrate, 0.01 g of copper (II) chloride dihydrate, and 1 L of distilled water.

In addition, the medium may also contain other ingredients which have not been enumerated herein, to an extent that would not impair the effect of the present invention.

The conditions for sterilizing the medium may be appropriately selected according to the type of the medium. For example, if the above-mentioned ME medium is used, this can be sterilized by steam at 100 to 130° C. for 5 to 15 minutes. Moreover, if any additive is to be added to the medium after sterilization, the additive has to be sterilized in advance by filtration or such a sterilization treatment.

The culture conditions, such as the pH of the medium, the concentration of the selenium acid compound in the medium, the incubation temperature, and the incubation time, are not specifically limited as long as JPCC SEP JP-1, JPCC SEP JP-2, or JPCCY SEP-3 can grow well.

For example, if the above-mentioned ME medium is used, the pH of the medium is preferably from 5.8 to 7.2, and more preferably from 6.0 to 6.5.

The concentration of the selenium acid compound in the medium is preferably from 5 to 80 ppm, and more preferably from 20 to 60 ppm.

The incubation temperature is preferably from 15 to 38° C., more preferably from 25 to 37° C., and particularly preferably from 25 to 35° C.

The incubation time can be appropriately selected according to the state of growth, it is preferably 20 hours or longer, and more preferably 30 hours or longer.

In addition, because JPCC SEP JP-1, JPCC SEP JP-2, and JPCCY SEP-3 are anaerobic, it is preferable to culture them while replacing the gas phase with argon gas or the like.

The acquired JPCC SEP R-1, JPCC SEP JP-2, or JPCCY SEP-3 are further preferably subjected to a preculture and a main culture. The medium and the culture conditions to be employed herein are the same as those mentioned above. However, the selenium acid compound is not always necessary. Moreover, the inoculation amounts of these microorganisms into the medium are not specifically limited, the inoculation is preferably carried out so that the concentration in the medium becomes about $1.0 \times 10^6$ to $1.0 \times 10^8$ cells/ml, for example.

Identification of JPCC SEP JP-1

JPCC SEP JP-1 was identified by TechnoSuruga Laboratory on consignment. Then, the acquired specimen was subjected to the validation of "morphological properties", "culturing properties", "physiological properties", "acid/gas productions from saccharides", and "other physiological properties", and the identification and phylogenetic analysis of "nucleotide sequence". The "morphological properties" are shown in Table 1. The "culturing properties" are shown in Table 2. The physiological properties" are shown in Table 3. The "acid/gas productions from saccharides" are shown in Table 4. The "other physiological properties" are shown in Table 5.

In Table 1 to Table 5, the items of (1) "Gelatin liquefaction" and "Gram staining property" were obtained with reference to the document "BARROW, (G. I.) and FELTHAM, (R. K. A): Cowan and Steel's Manual for the Identification of Medical Bacteria, 3rd edition, 1993, Cambridge University Press".

Moreover, the items of (2) "Culture condition with litmus milk", "MR test", "Hydrolysis of starch", "Utilization of citrate", "Utilization of inorganic nitrogen source", "Catalase", "Oxidase", "O-F test (oxidation/fermentation)", and "Acid/gas productions from saccharides" were obtained with reference to the document "Toshikazu Sakazaki, Etsuro Yoshizaki, and Kanji Miki: Shin Saikin Baichigaku Kouza (The Course of Culturing Medium for Microorganism), the latter volume, 2nd Edition, 1998, Kindai Shuppan, (Kinki University Press), Tokyo".

Furthermore, the items of (3) "Nitrate reduction", "Denitrification", "VP test", "Indol production", "Generation of hydrogen sulfide", "Urease activity", and "Other physiological properties" were obtained by using the "Bacterium Identification Kit API20E (bioMerieux, France)".

TABLE 1

(Morphological properties)

| | |
|---|---|
| Culture condition | Nutrient agar medium at 30° C. |
| Shape of cell | Rod shape (0.6-0.8 × 1.5-2.0 μm) |
| Presence/absence of cell pleomorphism | − |
| Motility (adhesion status of flagellum) | + (polar flagellum) |
| Presence/absence of spore (site of spore) | − |

TABLE 2

(Culturing properties)

| | |
|---|---|
| Culture condition | Nutrient agar medium at 30° C. |
| Color | Pale yellow |
| Glossiness | + |
| Pigment production | − |
| Culture condition | Nutrient broth medium at 30° C. |
| Presence/absence of surface growth | − |
| Presence/absence of turbidity in medium | + |
| Culture condition | Gelatin stab culture at 30° C. |
| Growth status | + |
| Gelatin liquefaction[1] | + |
| Culture condition[2] | Litmus milk at 30° C. |
| Solidification | − |
| Liquefaction | − (acidified) |

TABLE 3

(Physiological properties)

| | |
|---|---|
| Gram staining property[1] | − |
| Nitrate reduction[3] | + |
| Denitrification[3] | − |
| MR test[2] | + |

TABLE 3-continued (Physiological properties)

| | | |
|---|---|---|
| VP test[3] | | + |
| Indol production[3] | | + |
| Generation of hydrogen sulfide[3] | | − |
| Hydrolysis of starch[2] | | + |
| Utilization of citrate[2] | (Koser) | + |
| | (Christensen) | + |
| Utilization of inorganic nitrogen source[2] | Nitrate salt | + |
| | Ammonium salt | + |
| Urease activity[3] | | − |
| Catalase[2] | | + |
| Oxidase[2] | | + |
| Growth Range pH | 5 | + |
| | 8 | + |
| | 9 | + |
| Growth Range Temperature (° C.) | 15 | + |
| | 20 | + |
| | 37 | + |
| | 45 | + |
| Anaerobic viability | | + |
| O-F test (oxidation/fermentation)[2] | | +/+ |

TABLE 4

(Acid/gas productions from saccharides[2])

| | |
|---|---|
| L-arabinose | −/− |
| D-glucose | +/− |
| D-fructose | +/− |
| Maltose | +/− |
| Lactose | −/− |
| D-sorbitol | −/− |
| Inositol | −/− |
| D-xylose | −/− |
| D-mannose | +/− |
| D-galactose | +/− |
| Sucrose | +/− |
| Trehalose | +/− |
| D-mannitol | +/− |
| Glycerin | +/− |

TABLE 5

(Other physiological properties[3])

| | |
|---|---|
| β-galactosidase activity | + |
| Arginine dihydrolase activity | + |
| Lysine decarboxylase activity | − |
| Tryptophan deaminase activity | − |
| Gelatinase activity | + |

(Nucleotide Sequence)

The 16S rDNA of JPCC SEP JP-1 was identified by a publicly known method, as a result of which it was shown to have the nucleotide sequence represented by SEQ ID NO: 1.

(Phylogenetic Analysis)

Using JPCC SEP JP-1 that had been aerobically cultured in the medium of the Nutrient agar (Oxoid) at 30° C. for 24 hours, DNA extraction was conducted according to the protocol of the InstaGene Matrix (Bio-Rad Laboratories), polymerase chain reaction (PCR) was conducted according to the protocol of the MicroSeq 500 16s rDNA Bacterial Identification PCR Kit (Applied Biosystems), cycle sequencing was conducted according to the protocol of the MicroSeq 500 16s rDNA Bacterial Identification Sequencing Kit (Applied Biosystems), and sequencing was conducted according to the protocol of the ABI PRISM 3100 Genetic Analyzer System (Applied Biosystems).

The analysis softwares used herein were the Auto Assembler (Applied Biosystems) and the Apollon (TechnoSuruga Laboratory). The nucleotide sequence from the 5' end to about the position 500 of the obtained 16S rDNA sequence was subjected to the molecular phylogenetic analysis by cross-checking with the nucleotide sequence information acquired from the bacterial type strain database Apollon DB (TechnoSuruga Laboratory) and the International nucleotide sequence database (GenBank/DDBJ/EMBL). The thus obtained molecular phylogenetic tree is shown in FIG. 1. In FIG. 1, the bar on the bottom left is a scale bar and the reference symbol "T" at the end of a strain name indicates that the strain is a type strain of the species.

As a result of the homology search with respect to the bacterial type strain database using BLAST (refer to ALTSCHUL, (S. F.), MADDEN, (T. F.), SCHAFFER, (A. A.), ZHANG, (J.), ZHANG, (Z.), MILLER, (W.), and LIPMAN, (D. J.), Nucleic Acids Research, 1997, 25: 3389-3402), the above-mentioned partial sequence of the 16S rDNA sequence of JPCC SEP JP-1 showed a high homology with the 16S rDNA sequence derived from *Aeromonas*, and showed the highest homology of 99.6% with the 16S rDNA sequence of *Aeromonas punctata* strain ATCC15468. In the homology search with respect to the International nucleotide sequence database, it showed a high homology with the 16S rDNA sequence derived from *Aeromonas*, and showed a homology of 99.6% with the 16S rDNA sequence of *Aeromonas punctata* strain ATCC15468.

As a result of the molecular phylogenetic analysis, JPCC SEP JP-1 formed the same phylogenetic branch as that of *Aeromonas punctata* AY987728.1, *Aeromonas* sp. RK217215 AY987764.1, and *Aeromonas* sp. M10 DQ200865.1. However, as will be described later, JPCC SEP JP-1 showed apparently different physiological properties from these microorganisms, such as an ability to reduce selenium acid compounds. Thus, JPCC SEP JP-1 was deemed to be a novel species of the genus *Aeromonas*.

Identification of JPCC SEP JP-2

JPCC SEP JP-2 was identified by TechnoSuruga Laboratory on consignment in the same manner as that of JPCC SEP JP-1 mentioned above. The "morphological properties" of JPCC SEP JP-2 are shown in Table 6. The "culturing properties" are shown in Table 7. The "physiological properties" are shown in Table 8. The "acid/gas productions from saccharides" are shown in Table 9. The "other physiological properties" are shown in Table 10.

TABLE 6

(Morphological properties)

| | |
|---|---|
| Culture condition | Nutrient agar medium at 30° C. |
| Shape of cell | Rod shape (0.7-0.8 × 1.0-1.2 μm) |
| Presence/absence of cell pleomorphism | − |
| Motility (adhesion status of flagellum) | − |
| Presence/absence of spore (site of spore) | − |

TABLE 7

(Culturing properties)

| | |
|---|---|
| Culture condition | Nutrient agar medium at 30° C. |
| Color | Cream color |
| Glossiness | + |
| Pigment production | − |
| Culture condition | Nutrient broth medium at 30° C. |

TABLE 7-continued (Culturing properties)

| | |
|---|---|
| Presence/absence of surface growth | − |
| Presence/absence of turbidity in medium | + |
| Culture condition | Gelatin stab culture at 30° C. |
| Growth status | + |
| Gelatin liquefaction[1] | − |
| Culture condition[2] | Litmus milk at 30° C. |
| Solidification | − |
| Liquefaction | − (acidified) |

TABLE 8

(Physiological properties)

| | | |
|---|---|---|
| Gram staining property[1] | | − |
| Nitrate reduction[3] | | + |
| Denitrification[3] | | + |
| MR test[2] | | − |
| VP test[3] | | + |
| Indol production[3] | | − |
| Generation of hydrogen sulfide[3] | | − |
| Hydrolysis of starch[2] | | − |
| Utilization of citrate[2] | (Koser) | + |
| | (Christensen) | + |
| Utilization of inorganic nitrogen source[2] | Nitrate salt | + |
| | Ammonium salt | + |
| Urease activity[3] | | − |
| Catalase[2] | | + |
| Oxidase[2] | | − |
| Growth Range pH | 5 | + |
| | 8 | + |
| | 9 | + |
| Growth Range Temperature (° C.) | 15 | + |
| | 20 | + |
| | 37 | + |
| | 45 | + |
| Anaerobic viability | | + |
| O-F test (oxidation/fermentation)[2] | | +/+ |

TABLE 9

(Acid/gas productions from saccharides[2])

| | |
|---|---|
| L-arabinose | +/− |
| D-glucose | +/+ |
| D-fructose | +/+ |
| Maltose | +/− |
| Lactose | +/− |
| D-sorbitol | +/+ |
| Inositol | +/− |
| D-xylose | +/− |
| D-mannose | +/+ |
| D-galactose | +/+ |
| Sucrose | +/+ |
| Trehalose | +/+ |
| D-mannitol | +/+ |
| Glycerin | +/+ |

TABLE 10

(Other physiological properties[3])

| | |
|---|---|
| β-galactosidase activity | + |
| Arginine dihydrolase activity | − |
| Lysine decarboxylase activity | − |
| Tryptophan deaminase activity | − |
| Gelatinase activity | − |

(Nucleotide Sequence)

The 16S rDNA of JPCC SEP JP-2 was identified by a publicly known method, as a result of which it was shown to have the nucleotide sequence represented by SEQ ID NO: 2.

(Phylogenetic Analysis)

The molecular phylogenetic analysis of JPCC SEP JP-2 was conducted in the same manner as that of JPCC SEP JP-1 mentioned above. The thus obtained molecular phylogenetic tree is shown in FIG. 1.

As a result of the homology search with respect to the bacterial type strain database using BLAST (refer to ALTS-CHUL, (S. F.), MADDEN, (T. F.), SCHAFFER, (A. A.), ZHANG, (J.), ZHANG, (Z.), MILLER, (W.), and LIPMAN, (D. J.), Nucleic Acids Research, 1997, 25: 3389-3402), the partial sequence of the 16S rDNA sequence of JPCC SEP JP-2 showed a high homology with the 16S rDNA sequence derived from *Klebsiella*, and showed the highest homology of 99.8% with the 16S rDNA sequence of *Klebsiella variicola* F2R9 AJ783916.1. In addition, it also showed a homology of 99.0% with the 16S rDNA sequence derived from *Klebsiella pneumoniae*. In the homology search with respect to the International nucleotide sequence database, it showed a high homology with the 16S rDNA sequence derived from *Klebsiella pneumoniae*.

As a result of the molecular phylogenetic analysis, JPCC SEP JP-2 solely formed a phylogenetic branch outside the phylogenetic branch of the *Klebsiella variicola* F2R9 AJ783916.1 and *Klebsiella* sp. P2 AB114634.1, and also outside the phylogenetic branch of the *Klebsiella* sp. strain zmmo U31075.1 and *Klebsiella* sp. strain zmvsy U31076.1. Moreover, JPCC SEP JP-2 showed apparent differences in the physiological properties from known microorganisms of the genus *Klebsiella*, such as an ability to reduce selenium acid compounds. Thus, JPCC SEP JP-2 was determined to be a novel species of the genus *Klebsiella*.

Identification of JPCCY SEP-3

JPCCY SEP-3 was identified by TechnoSuruga Laboratory on consignment. Then, the acquired specimen was subjected to the validation of "morphological properties" "culturing properties", "physiological properties", and "acid/gas productions from saccharides". The results are shown in Table 11. Then, the specimen was subjected to the identification and phylogenetic analysis of "nucleotide sequence".

In Table 11, the items of (4) "Catalase reaction", "Oxidase reaction", and "Acid/gas productions from glucose" were obtained with reference to the document "BARROW, (G. I.) and FELTHAM, (R. K. A): Cowan and Steel's Manual for the Identification of Medical Bacteria, 3rd edition, 1993, Cambridge University Press".

In addition, the item of (5) "Gram staining property" was obtained by using the Favor-G "Nissui" (Nissui Pharmaceutical).

Moreover, the morphological observation was conducted by using the optical microscope BX50F4 (Olympus).

TABLE 11

(Morphological properties, culturing properties, physiological properties, and acid/gas productions from saccharides)

| | |
|---|---|
| Culture condition | Anaerobic culture in Agar medium 1 (described below) at 30° C. for 48 hours |
| Shape of cell | Rod shape (0.8 × 1.5-2.0 μm) |
| Motility | − |
| Presence/absence of spore | − |
| Diameter | 2.0-3.0 mm |
| Color tone | Cream color |
| Form | Circular |

TABLE 11-continued (Morphological properties, culturing properties, physiological properties, and acid/gas productions from saccharides)

| | |
|---|---|
| State of protrusion | Lenticular |
| Margin | Entire margin |
| Surface shape etc. | Smooth |
| Transparency | Semitransparent |
| Stickiness | Sticky |
| Gram staining property[5] | − |
| Incubation 37 | + |
| temperature (° C.) 45 | + |
| Catalase[4] | +w |
| Oxidase[4] | − |
| Acid/gas productions from glucose[4] | +/+ |

+w: weak reaction

Agar medium 1; A medium at pH 6.5 to 7.0 prepared by using glucose instead of lactic acid in the liquid ME medium mentioned above, and then added 15 g of agar thereto.

(Nucleotide Sequence)

The 16S rDNA of JPCCY SEP-3 was identified by a publicly known method, as a result of which it was shown to have the nucleotide sequence represented by SEQ ID NO: 3.

(Phylogenetic Analysis)

Figure 2:
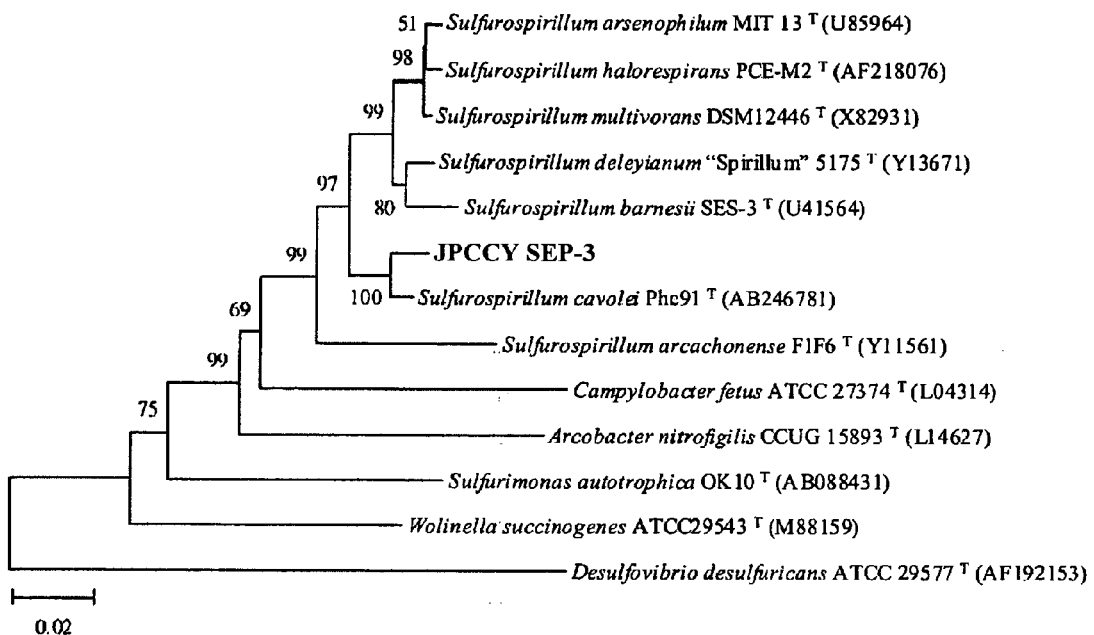
FIG. 2 is a molecular phylogenetic tree showing the result of the molecular phylogenetic analysis on the 16S rDNA of JPCCY SEP-3.

The analysis software used herein was the Apollon 2.0 (TechnoSuruga Laboratory). The obtained 16S rDNA sequence was subjected to the molecular phylogenetic analysis by cross-checking with the nucleotide sequence information acquired from the Apollon DB-BA 3.0 (TechnoSuruga Laboratory) and the International nucleotide sequence database (GenBank/DDBJ/EMBL). The thus obtained molecular phylogenetic tree is shown in FIG. 2. In FIG. 2, the bar on the bottom left is a scale bar and the reference symbol "T" at the end of a strain name indicates that the strain is a type strain of the species. The numerical value at each node of branches shows the bootstrap value.

As a result of the homology search with respect to the Apollon DB-BA 3.0 by using BLAST (refer to ALTSCHUL, (S. F.), MADDEN, (T. F.), SCHAFFER, (A. A.), ZHANG, (J.), ZHANG, (Z.), MILLER, (W.), and LIPMAN, (D. J.), Nucleic Acids Research, 1997, 25: 3389-3402), the 16S rDNA sequence of JPCCY SEP-3 showed a high homology with the 16S rDNA sequence derived from *Sulfurospirillum*, and showed the highest homology of 96.4% with the 16S rDNA sequence of *Sulfurospirillum deleyianum* strain *Spirillum* 5175 (refer to VALIDATION LIST No 44. Int. j. Syst. Bacteriol., 1993, 43, 188-189). In addition, in the homology search with respect to the International nucleotide sequence database, JPCCY SEP-3 showed a high homology with the 16S rDNA sequence derived from *Sulfurospirillum*, and showed the highest homology of 98.6% with the 16S rDNA sequence of *Sulfurospirillum cavolei* strain Phe91 (refer to KODAMA (Y.), HA (L. T.), and WATANABE (K.), Int. j. Syst. Evol. Microbiol., 2007, 57, 827-831). From these results, it was considered that JPCCY SEP-3 can highly possibly belong to the genus *Sulfurospirillum*. Therefore, a molecular phylogenetic tree was created by having 16S rDNAs from type strains, especially around a total of seven kinds of type strains belonging to the genus *Sulfurospirillum*, together with several type strains from the genus *Campylobacter*, the genus *Agrobacterium*, and the like which are relatively close to the genus *Sulfurospirillum*.

As a result of the molecular phylogenetic analysis, JPCCY SEP-3 appeared in the cluster of *Sulfurospirillum*, and formed the same phylogenetic branch as that of *Sulfurospirillum cavolei*. The bootstrap value which indicates the reliability of the phylogenetic branch (divergence) of JPCCY SEP-3 was shown to be 100%, and phylogenetic branches of other strains of *Sulfurospirillum* around JPCCY SEP-3 also showed relatively high bootstrap values. Therefore, these phylogenetic branches were considered to be highly stable. From these results, JPCCY SEP-3 was considered to belong to the genus *Sulfurospirillum*, and most closely related to *Sulfurospirillum cavolei*, among species as far as known. However, since the 16S rDNA sequences of both parties are not completely identical, both parties are not likely to be the same species in terms of the phylogenetic branches. Thus, JPCCY SEP-3 was determined to be a novel species of the genus *Sulfurospirillum*.

The JPCC SEP JP-1 of the present invention was deposited with the National Institute of Technology and Evaluation, Patent Microorganisms Depositary (2-5-8 Kazusakamatari, Kisarazu-shi, Chiba, Zip Code 292-0818, Japan) as of Mar. 23, 2007 with the accession number of NITE BP-345.

The JPCC SEP JP-2 of the present invention was deposited with the National Institute of Technology and Evaluation, Patent Microorganisms Depositary (2-5-8 Kazusakamatari, Kisarazu-shi, Chiba, Zip Code 292-0818, Japan) as of Mar. 23, 2007 with the accession number of NITE BP-346.

The JPCCY SEP-3 of the present invention was deposited with the National Institute of Technology and Evaluation, Patent Microorganisms Depositary (2-5-8 Kazusakamatari, Kisarazu-shi, Chiba, Zip Code 292-0818, Japan) as of Jun. 4, 2008 with the accession number of NITE BP-582.

Novel Microorganisms

The first microorganism of the present invention is *Aeromonas* sp. strain JPCC SEP JP-1. Moreover, the present invention also includes: a microorganism belonging to a species to which an *Aeromonas* sp. strain JPCC SEP JP-1 belongs; and a microorganism belonging to the genus *Aeromonas*, which has an ability to reduce a selenium acid compound, and the 16S rDNA sequence of which consists of a nucleotide sequence having a 96% or higher homology with the nucleotide sequence represented by SEQ ID NO: 1. Such microorganisms can be considered to be the same kind of microorganisms as the *Aeromonas* sp. strain JPCC SEP JP-1. Hereunder, such microorganisms and the *Aeromonas* sp. strain JPCC SEP JP-1 may be collectively referred to as the first microorganism group.

Regarding microorganisms belonging to the genus *Aeromonas*, *Aeromonas salmonicida* has been known which has an ability to reduce selenite ions into metallic selenium. However, neither close species of the *Aeromonas* sp. strain JPCC SEP JP-1 as a matter of course, nor any other microorganism belonging to the genus *Aeromonas*, have been known which have an ability to reduce selenium acid compounds so far. In addition, the first microorganism group of the present invention has a particularly high ability to reduce selenite ions into metallic selenium.

The second microorganism of the present invention is *Klebsiella* sp. strain JPCC SEP JP-2. Moreover, the present invention also includes: a microorganism belonging to a species to which a *Klebsiella* sp. strain JPCC SEP JP-2 belongs; and a microorganism belonging to the genus *Klebsiella*, which has an ability to reduce a selenium acid compound, and the 16S rDNA sequence of which consists of a nucleotide sequence having a 96% or higher homology with the nucleotide sequence represented by SEQ ID NO: 2.

Such microorganisms can be considered to be the same kind of microorganisms as the of the *Klebsiella* sp. strain JPCC SEP JP-2. Hereunder, such microorganisms and the *Klebsiella* sp. strain JPCC SEP JP-2 may be collectively referred to as the second microorganism group.

Regarding microorganisms belonging to the genus *Klebsiella*, no microorganism has been known which has an ability to reduce selenium acid compounds. In addition, the second microorganism group of the present invention has an ability to reduce both selenate ion and selenite ion into metallic selenium, and normally has a higher ability to reduce selenate ions into metallic selenium than that of the above-mentioned first microorganism group.

The third microorganism of the present invention is *Sulfurospirillum* sp. strain JPCCY SEP-3. Moreover, the present invention also includes: a microorganism belonging to a species to which a *Sulfurospirillum* sp. strain JPCCY SEP-3 belongs; and a microorganism belonging to the genus *Sulfurospirillum*, which has an ability to reduce a selenium acid compound, and the 16S rDNA sequence of which consists of a nucleotide sequence having a 96% or higher homology with the nucleotide sequence represented by SEQ ID NO: 3. Such microorganisms can be considered to be the same kind of microorganisms as the *Sulfurospirillum* sp. strain JPCCY SEP-3. Hereunder, such microorganisms and the *Sulfurospirillum* sp. strain JPCCY SEP-3 may be collectively referred to as the third microorganism group.

Regarding microorganisms belonging to the genus *Sulfurospirillum*, *Sulfurospirillum barnesii* has been known which has an ability to reduce selenium acid compounds. However, neither close species of the *Sulfurospirillum* sp. strain JPCCY SEP-3 as a matter of course, nor any other microorganism belonging to the genus *Sulfurospirillum*, have been known which have an ability to reduce selenium acid compounds so far. In addition, the third microorganism group of the present invention has a particularly high ability to reduce selenate ions into metallic selenium, and normally has this ability higher than those of the above-mentioned first and second microorganism groups.

Selenium Acid Compound-Reducing Agent

The selenium acid compound-reducing agent of the present invention comprises, as an active ingredient, at least one kind of microorganism(s) selected from the group consisting of the first microorganism group, the second microorganism group, and the third microorganism group, mentioned above. Of these, preferred is an agent comprising at least one kind of microorganism(s) selected from the first microorganism group, at least one kind of microorganism(s) selected from the second microorganism group, and at least one kind of microorganism(s) selected from the third microorganism group all together, and particularly preferred is an agent comprising JPCC SEP JP-1, JPCC SEP JP-2, and JPCCY SEP-3.

The selenium acid compound-reducing agent has a higher ability to reduce selenium acid compounds when it comprises a plurality of kinds of microorganisms from different microorganism groups than the case where it comprises only a single kind of microorganism of the present invention, or the case where it comprises a plurality of kinds of microorganisms only from the same microorganism group.

When the reducing agent comprises a plurality of kinds of microorganisms from different microorganism groups, the blending ratios of these microorganisms (for example, a microorganism from the first microorganism group, a microorganism from the second microorganism group, and a microorganism from the third microorganism group) can be appropriately selected according to the purpose.

The selenium acid compound-reducing agent can be prepared by either directly using, or after drying, a filtrated product produced by filtration of a culture solution yielded by culturing the microorganism(s) of the present invention, for example. Alternatively, the agent can also be prepared by purification of the cultured microorganism(s) of the present invention. Moreover, if necessary, this selenium acid compound-reducing agent may also contain various kinds of additives to an extent that would not impair the effect of the present invention. Furthermore, the microorganism(s) of the present invention may be immobilized on, for example: a natural polymeric gel such as agar and a gellan gum; acrylamide; a polymeric resin such as an ultraviolet curable resin; fibers such as carbon fibers, a hollow fiber membrane, and a nonwoven fabric; or the like. The immobilization can be achieved either by inclusion or immobilization on the surface.

Method for Reducing a Selenium Acid Compound

The method for reducing a selenium acid compound of the present invention comprises the step of culturing at least one kind of microorganism(s) selected from the group consisting of the first microorganism group, the second microorganism group, and the third microorganism group, mentioned above, under the presence of a selenium acid compound. Of these, it is preferable to co-culture at least one kind of microorganism(s) selected from the first microorganism group, at least one kind of microorganism(s) selected from the second microorganism group, and at least one kind of microorganism(s) selected from the third microorganism group all together, and it is particularly preferable to co-culture JPCC SEP JP-1, JPCC SEP JP-2, and JPCCY SEP-3 all together. The efficiency to reduce selenium acid compounds is higher when a plurality of kinds of microorganisms from different microorganism groups are co-cultured than the case where only a single kind of microorganism of the present invention is cultured, or the case where a plurality of kinds of microorganisms only from the same microorganism group are cultured.

When a plurality of kinds of microorganisms from different microorganism groups are co-cultured, the blending ratios of these microorganisms (for example, a microorganism from the first microorganism group, a microorganism from the second microorganism group, and a microorganism from the third microorganism group) is the same as the case of the selenium acid compound-reducing agent mentioned above.

For example, by co-culturing JPCC SEP JP-1, JPCC SEP JP-2, and JPCCY SEP-3 all together, selenium acid can be reduced into metallic selenium faster than the case where only a single kind of conventional microorganism having an ability to reduce selenium acid compounds is cultured, or the case where a plurality of kinds of such conventional microorganisms are co-cultured. For example, even in the case where a microorganism of the genus *Bacillus* that is considered to be one of the microorganisms having the fastest rate of reducing selenium acid compounds among microorganisms reported so far (refer to Japanese Unexamined Patent Application, First Publication No. H9-248595) is cultured, it takes about 100 hours to reduce selenate acid ions into metallic selenium completely. One of the main reasons for this is that the rate of reducing selenite ion into metallic selenium is slow. On the other hand, when JPCC SEP JP-1, JPCC SEP JP-2, and JPCCY SEP-3 are co-cultured all together, it takes only about 24 hours to completely reduce selenate ion into metallic selenium. This is because both the rate of reducing selenate ion into selenite ion and the rate of reducing selenite ion into metallic selenium are faster than conventional cases.

The amount of the microorganism(s) of the present invention for use in the reduction of a selenium acid compound varies depending on the environment where the reduction is carried out, it is preferable to increase the density of the microorganism(s) to an extent that would not impair the effect of the present invention, because it leads to a higher activity to reduce selenium acid compounds.

The conditions for culturing the microorganism(s) of the present invention upon reduction of a selenium acid compound are not specifically limited. For example, it is preferable to conduct the culture by referring to the above-mentioned culture conditions at the time of the acquisition of the microorganism(s). Moreover, upon reduction of a selenium acid compound contained in an object such as waste water, soil, sludge, underground water, and water in a reservoir, it is preferable to conduct the culture by using a medium which contains appropriate amounts of the above-mentioned ingredients which are necessary for the growth of the microorganism(s) of the present invention, as well as referring to the above-mentioned culture conditions at the time of the acquisition of the microorganism(s) regarding the other culture conditions.

The inoculation of the microorganism(s) of the present invention is preferably conducted by adding the above-mentioned selenium acid compound-reducing agent, or by adding the preculture product of the microorganism(s) of the present invention. The amount of addition can be determined by considering the content of the microorganism(s) of the present invention in the reducing agent or the preculture product.

Method for Removing a Selenium Acid Compound

The method for removing a selenium acid compound of the present invention comprises the step of culturing at least one kind of microorganism(s) selected from the group consisting of the first microorganism group, the second microorganism group, and the third microorganism group, mentioned above, under the presence of a selenium acid compound.

The conditions for inoculating or culturing the microorganism(s) of the present invention may be the same as the conditions described in the method for reducing a selenium acid compound.

In addition, by inoculating an appropriate amount of the microorganism(s) of the present invention into the medium containing the object of the removal of the selenium acid compound, and culturing it(them) therein, the selenium acid compound can be taken into the microorganism(s) and the thus taken selenium acid compound can be reduced into metallic selenium. Therefore, by removing this with a known method such as filtration, the selenium acid compound can be efficiently removed from the object of the removal.

Process for Producing Metallic Selenium

The process for producing metallic selenium of the present invention comprises the steps of: culturing at least one kind of microorganism(s) selected from the group consisting of the first microorganism group, the second microorganism group, and the third microorganism group, mentioned above, under the presence of a selenium acid compound; and separating the thus produced culture product.

The step of culturing the microorganism(s) under the presence of a selenium acid compound can be conducted by the method described in the method for removing a selenium acid compound, for example. In addition, the yield of the metallic selenium can be increased by selecting a method that would lead to a higher efficiency to reduce selenium acid compounds.

Regarding the step of separating the produced culture product, the separation method is not specifically limited, and may be appropriately selected according to the kind of the object of the removal of the selenium acid compound, for example. Specifically, there can be employed filtration with a filter, or solid-liquid separation with a centrifugal machine. Since the thus separated filtrate contains the microorganisms of the present invention which contain metallic selenium inside of their bodies, the metallic selenium can be collected from these bacterial bodies. The collection method may be any one of known methods which can break down the bacterial bodies as long as the method would not cause any reaction of the metallic selenium. The method can be exemplified by the collection of metallic selenium by means of thermal decomposition of bacterial bodies. Organic matters constituting the bacterial bodies can be decomposed into $CO_2$ by heating the bacterial bodies, and then metallic selenium can be collected from the yielded residue.

The microorganisms of the present invention do exhibit the same effect to compounds of tellurium, which is a metallic element in the same group of selenium, specifically to, tellurium acid compounds such as telluric acid ($H_2TeO_4$), tellurous acid ($H_2TeO_3$), salts thereof, and ions thereof ($TeO_4^{2-}$ or $TeO_3^{2-}$). That is, it is possible to intake and reduce them into metallic tellurium. Therefore, a tellurium acid compound-reducing agent, a method for reducing a tellurium acid compound, a method for removing a tellurium acid compound, and a process for producing metallic tellurium using the microorganism(s) of the present invention are also included in the inventive aspects of this application. Here, the term tellurium acid compound refers to telluric acid, tellurous acid, salts thereof, and ions thereof.

EXAMPLES

Hereunder is a more detailed description of the present invention with specific Examples. However, the present invention is in no way limited to the following Examples.

Example 1

(Acquisition of JPCC SEP JP-1, JPCC SEP JP-2, and JPCCY SEP-3)

The above-mentioned ME medium (pH 6.5 to 7.0) was sterilized by steam at 121° C. for 10 minutes. Next, in a clean bench, 20 ml of the steam-sterilized ME medium was poured into a 30 ml volume vial container which had been sterilized by dry heating at 180° C. for 20 minutes. Then, 10000 ppm selenic acid which had been sterilized by filtration with a 0.22 μm filter was added thereto at a concentration of 50 ppm.

Subsequently, silt from a mangrove forest in Amami Island was added, and the container was sealed airtight by closing with a butyl rubber stopper and an aluminum cap. After the airtight sealing, argon gas which had been sterilized by filtration with a 0.22 μm filter was blown inside the medium to effect deaeration of the medium.

Next, the medium was incubated at 25° C. Then, vial containers in which the culture solution turned to red during 2 to 7 days were selected. From the selected vial containers, 100 μl of the culture solution was drawn and diluted 100-fold, 1000-fold, and 10000-fold, with the above-mentioned sterilized ME medium. The diluted solution was applied to an agar plate of the above-mentioned selenic acid-containing ME medium, by which microorganisms were cultured.

Thereafter, most quickly grown colonies were picked up and purified on an ME medium agar plate, as a result of which JPCC SEP JP-1, JPCC SEP JP-2, and JPCCY SEP-3 were acquired all together.

Example 2

(Evaluation 1 of Selenate Ion Removing Activity Upon the Co-Culture of JPCC SEP JP-1, JPCC SEP JP-2, and JPCCY SEP-3)

Similarly to Example 1, the sterilized ME medium containing 50 ppm of selenic acid was sealed up in a heat-dry sterilized 30 ml volume vial container, and argon gas which had been sterilized by filtration with a 0.22 μm filter was blown inside the medium to effect deaeration of the medium.

Next, the deaerated medium was inoculated with 2 volume % (0.4 ml) of the bacterial mixture of JPCC SEP JP-1, JPCC SEP JP-2, and JPCCY SEP-3 yielded from Example 1 by using a γ-ray sterilized needle syringe.

Then, the gas phase of the vial container was replaced with argon gas which had been sterilized by filtration with a 0.22 µm filter, by which these microorganisms were cultured under an anaerobic condition at 28° C. for 48 hours, yielding a preculture solution.

In a clean bench, 170 ml of the ME medium which had been sterilized by steam at 121° C. for 10 minutes was poured into a 200 ml volume glass container which had been sterilized under germicidal light for 10 minutes. Next, 10000 ppm selenic acid which had been sterilized by filtration with a 0.22 µm filter was added to the ME medium at a concentration of 1 mM (about 42 ppm). Then, 3 volume % (5 ml) of the preculture solution was inoculated therein.

After the inoculation, the glass container was covered with a top plate, and the gas phase of the container was replaced with argon gas which had been sterilized by filtration with a 0.22 µm filter, at a flow rate of 100 ml/minute for 5 minutes, by which the main culture was conducted under an anaerobic condition at 28° C.

Figure 3:
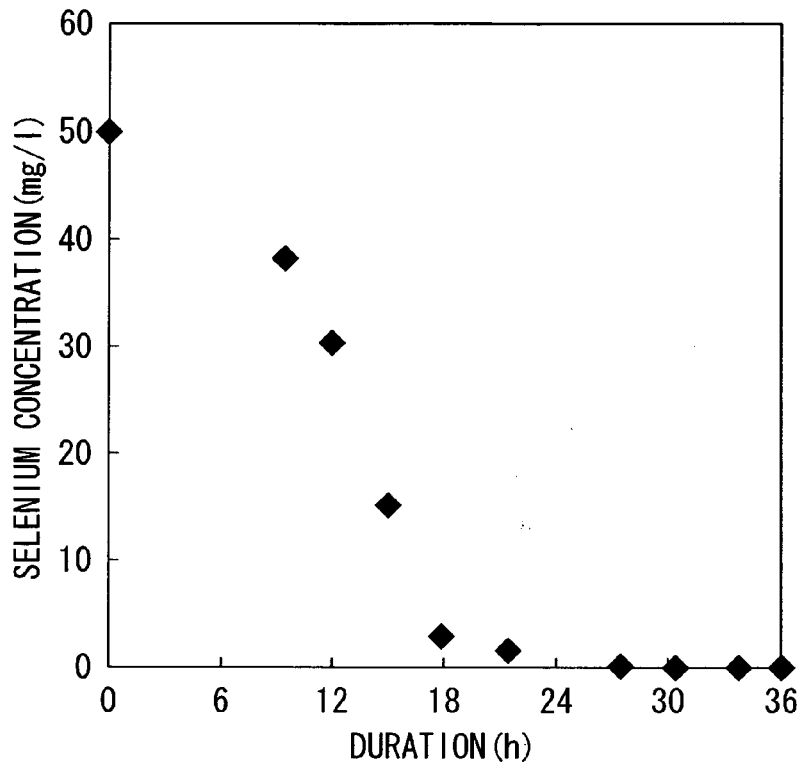
FIG. 3 is a graph showing the hexavalent and tetravalent selenium-removing activity in Example 2.

Then, the concentration of hexavalent and tetravalent selenium in the medium was measured by atomic absorption in a time course manner, so as to evaluate the selenic acid removing activity. The result is shown in FIG. 3. In FIG. 3, the y-axis indicates the total concentration of hexavalent and tetravalent selenium in the medium, and the x-axis shows the duration of the main culture.

As shown in FIG. 3, it was found that hexavalent and tetravalent selenium was almost completely removed from the medium approximately after 24 hours from the initiation of the main culture.

Figure 4:
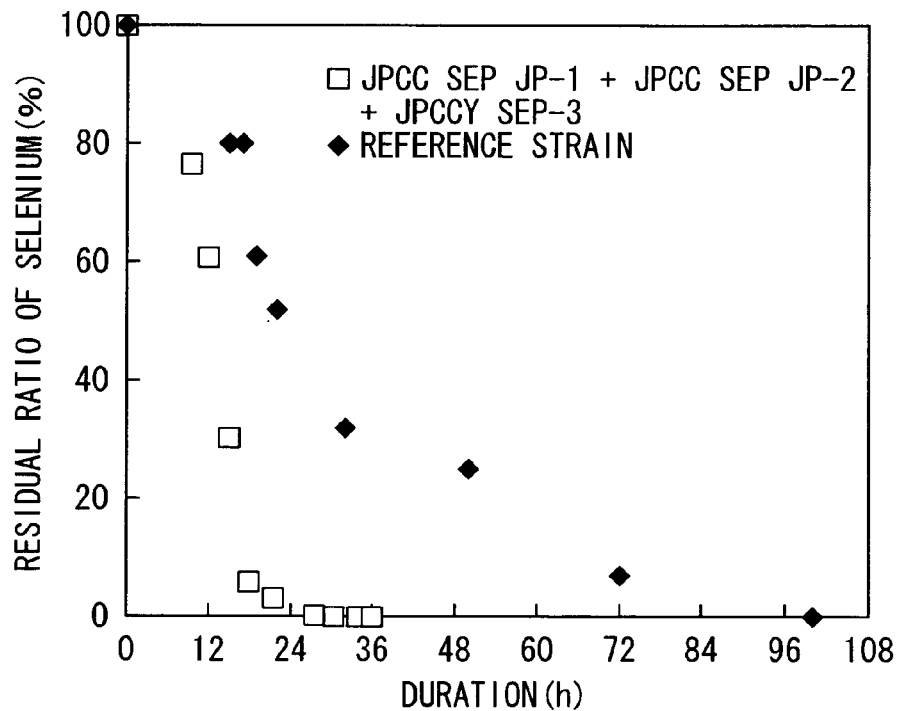
FIG. 4 is a graph collectively showing the hexavalent and tetravalent selenium-removing activities of a bacterial mixture of JPCC SEP JP-1 and JPCC SEP JP-2, and of a microorganism of the genus *Bacillus* (reference strain).

In addition, for the purpose of reference, data on the hexavalent and tetravalent selenium-removing activity of a microorganism of the genus *Bacillus* (reference strain) described in the document "Kashiwa M, Ike M, Mihara H, Esaki N, and Fujita M., Removal of soluble selenium by a selenate-reducing bacterium *Bacillus* sp. SF-1. Biofactors., 2001; 14(1-4): 261-5" is supplementally added and shown in FIG. 4 for the purpose of comparison with the data of this Example. The graph of FIG. 4 shows the hexavalent and tetravalent selenium-removing activities of these microorganisms in the same scale of axis, wherein the y-axis indicates the total residual ratio of hexavalent and tetravalent selenium in the medium, and the x-axis shows the duration of the main culture.

Because it is difficult to culture the bacterial mixture and the reference strain under the same conditions, their hexavalent and tetravalent selenium-removing activities can not be compared under the same conditions. However, the graph of FIG. 4 is sufficient to compare their best removing activities. As apparent from FIG. 4, the bacterial mixture comprising the microorganisms of the present invention was found to be able to completely remove hexavalent and tetravalent selenium within a time one-fourth or shorter of that of the reference strain.

Example 3

(Evaluation 2 of Selenate Ion Removing Activity Upon the Co-Culture of JPCC SEP JP-1, JPCC SEP JP-2, and JPCCY SEP-3)

Figure 5:
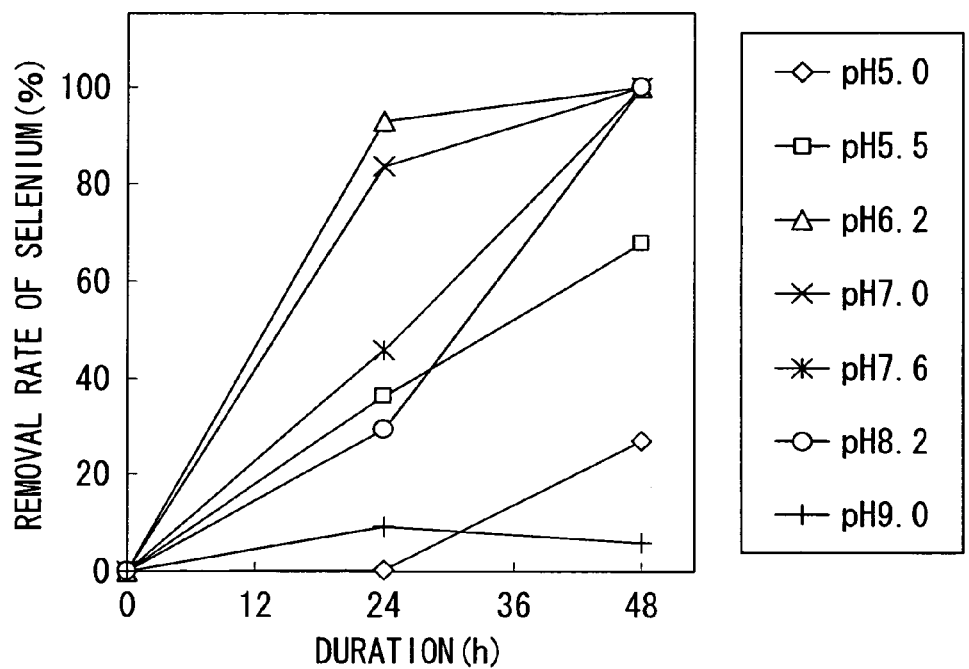
FIG. 5 is a graph showing the hexavalent and tetravalent selenium-removing activities in Example 3.

Similarly to Example 1, 30 ml of the sterilized ME medium containing 30 ppm of selenic acid with JPCC SEP JP-1, JPCC SEP JP-2, and JPCCY SEP-3 at a concentration of $1\times10^7$ cells/ml was sealed up in a heat-dry sterilized 30 ml volume vial container. The pH of the medium was adjusted at seven variations of 5.0, 5.5, 6.2, 7.0, 7.6, 8.2, and 9.0. The culture was carried out using these media at 25° C. for 48 hours. Then, the concentration of hexavalent and tetravalent selenium in each medium was measured by atomic absorption in a time course manner, so as to evaluate the selenic acid removing activity. The results are shown in FIG. 5. In FIG. 5, the y-axis indicates the total removal rate of hexavalent and tetravalent selenium in the medium, and the x-axis shows the duration of the culture.

As shown in FIG. 5, the removal rate was approximately 100% when the pH was 6.2, 7.0, and 7.6. The speed of removal was high when the pH was 6.2 and 7.0, and it was confirmed that the hexavalent and tetravalent selenium was able to be most quickly removed particularly when the pH was 6.2.

Example 4

(Evaluation 3 of Selenate Ion Removing Activity Upon the Co-Culture of JPCC SEP JP-1, JPCC SEP JP-2, and JPCCY SEP-3)

The selenic acid removing activity was evaluated in the same manner as that of Example 3, except that the pH of the medium was set at 6.2 and the incubation temperature was set at seven variations of 23, 28, 32, 37, 40, 45, and 60° C. The results are shown in FIG. 6.

Figure 6:
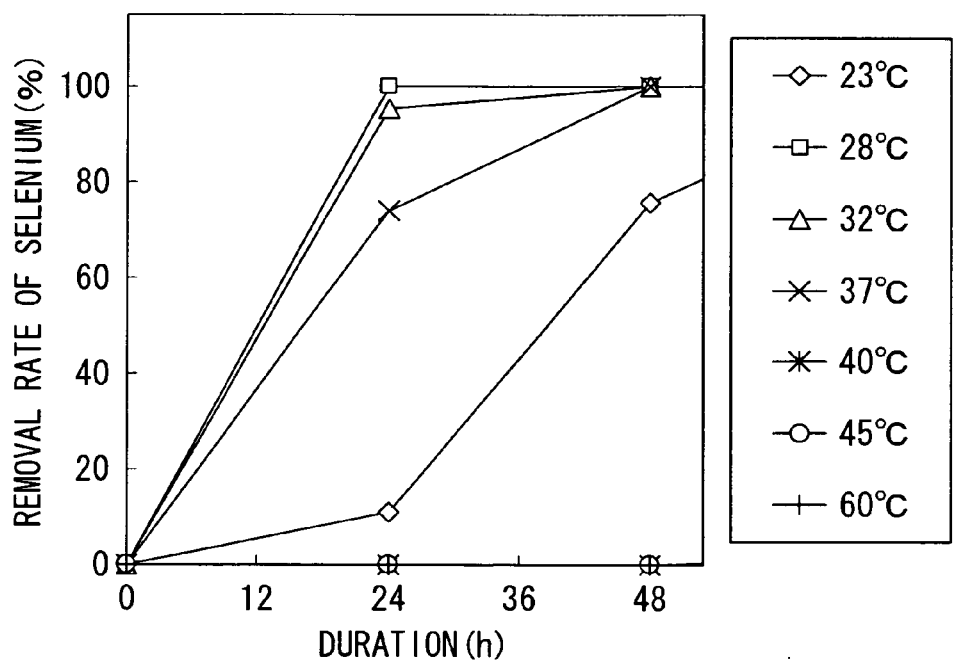
FIG. 6 is a graph showing the hexavalent and tetravalent selenium-removing activities in Example 4.

As shown in FIG. 6, the removal rate was approximately 100% when the temperature was 28, 32, and 37° C. The speed of removal was high when the temperature was 28 and 32° C., and it was confirmed that the hexavalent and tetravalent selenium was able to be most quickly removed particularly when the temperature was 28° C.

Example 5

(Evaluation 4 of Selenate Ion Removing Activity Upon the Co-Culture of JPCC SEP JP-1, JPCC SEP JP-2, and JPCCY SEP-3)

The selenic acid removing activity was evaluated in the same manner as that of Example 3, except that the medium was prepared by adding ethanol, methanol, ethanol+methanol, or acetic acid, as a carbon source, instead of lactic acid in the ME medium, the pH of the medium was set at 6.2, and the incubation temperature was set at 28° C. The evaluation was conducted with use of the ME medium at the same time. The results are shown in FIG. 7.

Figure 7:
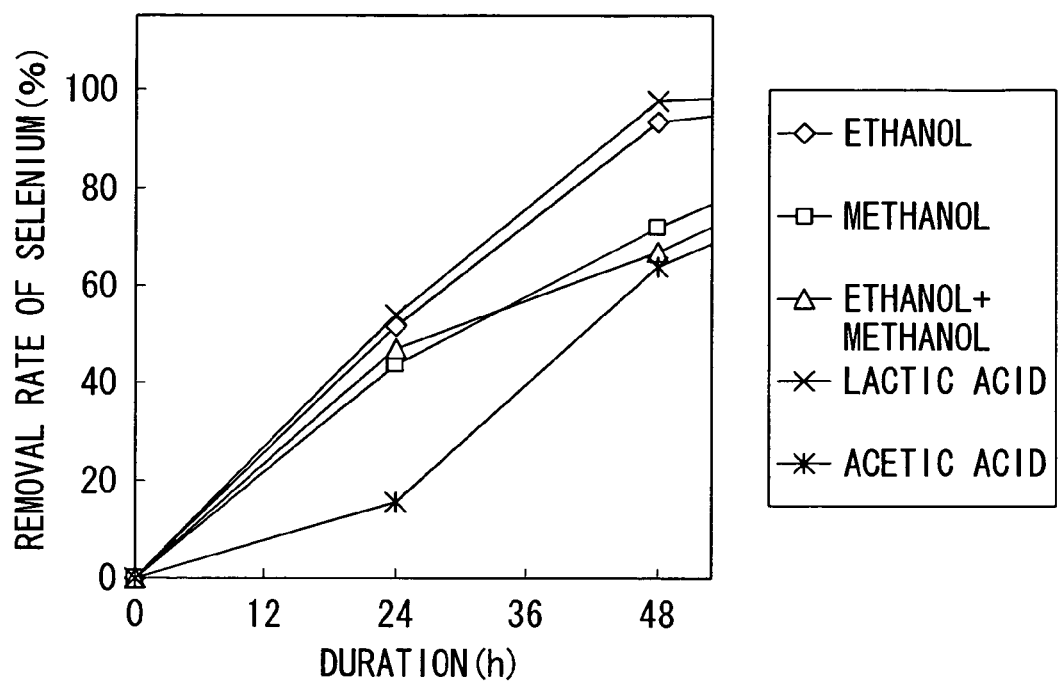
FIG. 7 is a graph showing the hexavalent and tetravalent selenium-removing activities in Example 5.

As shown in FIG. 7, the removal rate was significantly high when lactic acid or ethanol was used as a carbon source, and it was confirmed that the hexavalent and tetravalent selenium was able to be removed at the highest rate particularly when lactic acid was used.

Example 6

(Production of Metallic Selenium by JPCC SEP JP-1)

In the same manner as that of Example 1, 30 ml of the sterilized ME medium adjusted at pH 6.2 was poured into a 30 ml volume vial container which had been sterilized by dry heating. JPCC SEP JP-1 was inoculated therein and subjected to pure culture for 24 hours to thereby conduct the preculture.

Next, 30 ml of the ME medium was poured into a 30 ml volume sterilized vial container, to which selenate ion (hexavalent selenium) and selenite ion (tetravalent selenium) were added at the concentration of 50 ppm respectively. The medium was inoculated with 2 volume % of the preculture solution, and then the main culture was conducted (n=3). After 48 hours from the initiation of the main culture, the samples were filtrated with a 0.22 μm filter. In the recovered product on the filter, hexavalent and tetravalent selenium was quantified by an atomic absorption spectrophotometer, and the concentration (average value) of hexavalent and tetravalent selenium in the culture solution was obtained. Then, the recovery rate of metallic selenium was calculated from the following equation. The results are shown in Table 12.

(recovery rate of metallic selenium (%))=100−{(selenium concentration in culture solution (ppm))/50 (ppm)}×100

Example 7

(Production of Metallic Selenium by JPCC SEP JP-2)

The recovery rate of metallic selenium was calculated in the same manner as that of Example 6, except that JPCC SEP JP-2 was used instead of JPCC SEP JP-1. The results are shown in Table 12.

Example 8

(Production of Metallic Selenium by JPCCY SEP-3)

The recovery rate of metallic selenium was calculated in the same manner as that of Example 6, except that JPCCY SEP-3 was used instead of JPCC SEP JP-1. The results are shown in Table 12.

Example 9

(Production of Metallic Selenium by JPCC SEP JP-1 and JPCC SEP JP-2)

The recovery rate of metallic selenium was calculated in the same manner as that of Example 6, except that 1 volume % of a preculture solution of JPCC SEP JP-1 and 1 volume % of a preculture solution JPCC SEP JP-2 were inoculated, instead of inoculating 2 volume % of the preculture solution of JPCC SEP JP-1. The results are shown in Table 12.

Example 10

(Production of Metallic Selenium by JPCC SEP JP-1, JPCC SEP JP-2, and JPCCY SEP-3)

The recovery rate of metallic selenium was calculated in the same manner as that of Example 6, except that a total of 2 volume % of a preculture solution of JPCC SEP JP-1, a preculture solution JPCC SEP JP-2, and a preculture solution of JPCCY SEP-3 were inoculated, instead of inoculating 2 volume % of the preculture solution of JPCC SEP JP-1. The results are shown in Table 12.

TABLE 12

| Experimetnal plot | | Selenium species | Selenium concentration in culture solution (ppm) | Recovery rate of metallic selenium (%) |
|---|---|---|---|---|
| Example 6 | JPCC SEP JP-1 | Tetravalent | 37.0 ± 0.7 | 26.0 |
| | | Hexavalent | 51.4 ± 0.5 | 0 |
| Example 7 | JPCC SEP JP-2 | Tetravalent | 45.7 ± 0.2 | 8.6 |
| | | Hexavalent | 46.5 ± 0.3 | 7.0 |
| Example 8 | JPCCY SEP-3 | Tetravalent | 51.8 ± 0.4 | 0 |
| | | Hexavalent | 26.2 ± 3.2 | 52.4 |
| Example 9 | JPCC SEP JP-1 + JPCC SEP JP-2 | Tetravalent | 49.0 ± 0.0 | 2.0 |
| | | Hexavalent | 40.1 ± 0.3 | 19.8 |
| Example 10 | JPCC SEP JP-1 + JPCC SEP JP-2 + JPCCY SEP-3 | Tetravalent | N.D. | 100 |
| | | Hexavalent | N.D. | 100 |

All of JPCC SEP JP-1, JPCC SEP JP-2, and JPCCY SEP-3 had an ability to reduce selenium acid compounds, and it was confirmed that the ability to reduce hexavalent and tetravalent selenium was remarkably high when these three kinds of microorganisms were used all together.

INDUSTRIAL APPLICABILITY

The present invention is applicable to the removal of selenium acid compounds from waste water, soil, sludge, and the like.

[Accession Numbers]
NITE BP-345, NITE BP-346, and NITE BP-582

---

The invention claimed is:

1. A method for reducing a selenium acid compound, comprising the step of co-culturing *Aeromonas* JPCC SEP JP-1 (accession number NITE BP-345), *Klebsiella* JPCC SEP JP-2 (accession number NITE BP-346), and *Sulfurospirillum* JPCCY SEP-3 (accession number NITE BP-582), under the presence of a selenium acid compound.

2. A method for reducing a selenium acid compound, comprising the step of culturing *Sulfurospirillum* JPCCY SEP-3 (accession number NITE BP-582) under the presence of a selenium acid compound.

3. The method for reducing a selenium acid compound according to claim 1, wherein the step of co-culturing is performed under an anaerobic condition.

4. The method for reducing a selenium acid compound according to claim 3, wherein the step of co-culturing is performed at 28° C.

5. The method for reducing a selenium acid compound according to claim 2, wherein the step of co-culturing is performed under an anaerobic condition.

6. The method for reducing a selenium acid compound according to claim 5, wherein the step of co-culturing is performed at 28° C.

* * * * *

UNITED STATES PATENT AND TRADEMARK OFFICE
CERTIFICATE OF CORRECTION

PATENT NO. : 8,541,215 B2  Page 1 of 1
APPLICATION NO. : 12/737166
DATED : September 24, 2013
INVENTOR(S) : Matsumoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 216 days.

Signed and Sealed this

Fifteenth Day of September, 2015

Michelle K. Lee
*Director of the United States Patent and Trademark Office*

SEQUENCE LISTING

```
<160> NUMBER OF SEQ ID NOS: 3

<210> SEQ ID NO 1
<211> LENGTH: 1480
<212> TYPE: DNA
<213> ORGANISM: Aeromonas sp.
<220> FEATURE:
<221> NAME/KEY: misc_feature
<223> OTHER INFORMATION: strain JPCC SEP JP-1

<400> SEQUENCE: 1
ctcagattga acgctggcgg caggcctaac acatgcaagt cgagcggcag cgggaaagta        60
gcttgctact tttgccggcg agcggcggac gggtgagtaa tgcctgggaa attgcccagt       120 cgaggggat  aacagttgga aacgactgct aataccgcat acgccctacg ggggaaagca       180
ggggaccttc gggccttgcg cgattggata tgcccaggtg ggattagcta gttggtgagg       240
taatggctca ccaaggcgac gatccctagc tggtctgaga ggatgatcag ccacactgga       300
```

-continued

```
actgagacac ggtccagact cctacgggag gcagcagtgg ggaatattgc acaatggggg    360
aaaccctgat gcagccatgc cgcgtgtgtg aagaaggcct tcgggttgta aagcactttc    420
agcgaggagg aaaggtcagt agctaatatc tgctgactgt gacgttactc gcagaagaag    480
caccggctaa ctccgtgcca gcagccgcgg taatacggag ggtgcaagcg ttaatcggaa    540
ttactgggcg taaagcgcac gcaggcggtt ggataagtta gatgtgaaag ccccgggctc    600
aacctgggaa ttgcatttaa aactgtccag ctagagtctt gtagaggggg gtagaattcc    660
aggtgtagcg gtgaaatgcg tagagatctg gaggaatacc ggtggcgaag gcggcccct    720 ggacaaagac tgacgctcag gtgcgaaagc gtggggagca acaggatta gataccctgg    780 tagtccacgc cgtaaacgat gtcgatttgg aggctgtgtc cttgagacgt ggcttccgga    840
gctaacgcgt taaatcgacc gcctgggag tacggccgca aggttaaaac tcaaatgaat    900 tgacggggc ccgcacaagc ggtggagcat gtggtttaat tcgatgcaac gcgaagaacc    960
ttacctggcc ttgacatgtc tggaatcctg cagagatgcg ggagtgcctt cgggaatcag   1020
aacacaggtg ctgcatggct gtcgtcagct cgtgtcgtga gatgttgggt taagtcccgc   1080
aacgagcgca acccctgtcc tttgttgcca gcacgtaatg gtgggaactc aagggagact   1140
gccggtgata accggagga aggtggggat gacgtcaagt catcatggcc cttacggcca   1200
gggctacaca cgtgctacaa tggcgcgtac agagggctgc aagctagcga tagtgagcga   1260
atcccaaaaa gcgcgtcgta gtccggattg gagtctgcaa ctcgactcca tgaagtcgga   1320
atcgctagta atcgcaaatc agaatgttgc ggtgaatacg ttcccgggcc ttgtacacac   1380
cgcccgtcac accatgggag tgggttgcac cagaagtaga tagcttaacc ttcgggaggg   1440
cgtttaccac ggtgtgattc atgactgggg tgaagtcgta                         1480
```

<210> SEQ ID NO 2
<211> LENGTH: 1473
<212> TYPE: DNA
<213> ORGANISM: Klebsiela sp.
<220> FEATURE:
<221> NAME/KEY: misc_feature
<223> OTHER INFORMATION: strain JPCC SEP JP-2

<400> SEQUENCE: 2

```
tcagattgaa cgctggcggc aggcctaaca catgcaagtc gagcggtagc acagagagct     60
tgctctcggg tgacgagcgg cggacgggtg agtaatgtct gggaaactgc ctgatggagg    120
gggataacta ctggaaacgg tagctaatac cgcataacgt cgcaagacca agtgggggga    180
ccttcgggcc tcatgccatc agatgtgccc agatgggatt agctggtagg tggggtaacg    240
gctcacctag gcgacgatcc ctagctggtc tgagaggatg accagccaca ctggaactga    300
gacacggtcc agactcctac gggaggcagc agtgggaat attgcacaat gggcgcaagc    360
ctgatgcagc catgccgcgt gtgtgaagaa ggccttcggg ttgtaaagca ctttcagcgg    420
ggaggaaggc ggtgaggtta ataacctcat cgattgacgt tacccgcaga agaagcaccg    480
gctaactccg tgccagcagc cgcggtaata cggagggtgc aagcgttaat cggaattact    540
gggcgtaaag cgcacgcagg cggtctgtca gtcggatgt gaaatccccg gctcaaccct    600
gggaactgca ttcgaaactg gcaggctaga gtcttgtaga ggggggtaga attccaggtg    660
tagcggtgaa atgcgtagag atctggagga ataccggtgg cgaaggcggc ccctggaca    720 aagactgacg ctcaggtgcg aaagcgtggg gagcaaacag gattagatac cctggtagtc    780
```

```
cacgctgtaa acgatgtcga tttggaggtt gtgcccttga ggcgtggctt ccggagctaa    840
cgcgttaaat cgaccgcctg gggagtacgg ccgcaaggtt aaaactcaaa tgaattgacg    900
ggggcccgca caagcggtgg agcatgtggt ttaattcgat gcaacgcgaa gaaccttacc    960
tggtcttgac atccacagaa cttwscagag atgswttggt gccttcggga actgtgagac   1020
aggtgctgca tggctgtcgt cagctcgtgt tgtgaaatgt tgggttaagt cccgcaacga   1080
gcgcaaccct tatcctttgt tgccagcggt taggccggga actcaaagga gactgccagt   1140
gataaactgg aggaaggtgg ggatgacgtc aagtcatcat ggcccttacg accagggcta   1200
cacacgtgct acaatggcat atacaaagag aagcgacctc gcgagagcaa gcggacctca   1260
taaagtatgt cgtagtccgg attggagtct gcaactcgac tccatgaagt cggaatcgct   1320
agtaatcgta gatcagaatg ctacggtgaa tacgttcccg ggccttgtac acaccgcccg   1380
tcacaccatg ggagtgggtt gcaaaagaag taggtagctt aaccttcggg agggcgctta   1440
ccactttgtg attcatgact ggggtgaagt cgt                                1473

<210> SEQ ID NO 3
<211> LENGTH: 1432
<212> TYPE: DNA
<213> ORGANISM: Sulfurospirillum sp.
<220> FEATURE:
<221> NAME/KEY: misc_feature
<223> OTHER INFORMATION: strain JPCCY SEP-3

<400> SEQUENCE: 3
cagagtgaac gctggcggcg tgcttaacac atgcaagtcg aacgggttta aggagcttgc     60
ttcttaaatt agtggcgcac gggtgagtaa tgtatagcta atctgccctt tagtggggga    120
caacagttgg aaacgactgc taataccccca tactcctatt tatcacaaga tagataggga   180
aagatttatt gctaaaggat ggggctttat ggtatcagct agttggtggg gtaacggcct    240
accaaggcaa tgacgcctac ctggtctgag aggatgatca ggcacactgg aactgagaca    300
cggtccagac tcctacggga ggcagcagtg gggaatattg cacaatgggg gaaaccctga    360
tgcagcaacg ccgcgtggag gatgacgcat ttcggtgtgt aaactccttt tataagggaa    420
gataatgacg gtaccttatg aataagcacc ggctaactcc gtgccagcag ccgcggtaat    480
acggagggtg caagcgttac tcggaatcac tgggcgtaaa ggatgcgtag ctgtgatat     540
aagtcagaag tgaaatccaa cggcttaacc gttgaactgc ttttgaaact gtttcactag    600
aatatgggag aggtagatgg aattggtggt gtagggtaa atccgtaga tatcaccagg     660
aataccgatt gcgaaggcga tctactggaa cattattgac gctgaggcat gaaagcgtgg    720
ggagcaaaca ggattagata ccctggtagt ccacgcccta acgatgcac actagttgtt     780
gcgatgctag tcattgcagt aatgcactta acagattaag tgtgccgcct ggggagtacg    840
gtcgcaagat taaaactcaa aggaatagac ggggaccccgc acaagcggtg gagcatgtgg   900
tttaattcga agatacacga gaaccttac ctgggcttga tatccttgga atcttgtaga    960
gatacgagag tgctagtttta ctagaaccaa gagacaggtg ctgcacggct gtcgtcagct   1020
cgtgtcgtga gatgttgggt taagtcccgc aacgagcgca accctcgtga ttagttgcta   1080
acggtttggc cgagcactct aatcagactg ccttcgcaag gaggaggaag gtgaggacga   1140
cgtcaagtca tcatggccct tatgcccagg gctacacacg tgctacaatg gcgcgtacaa   1200
```

```
agagaagcga tactgtgaag tggagcaaat cttaaaaacg cgtctcagtt cggattggag    1260
tctgcaactc gactccatga agctggaatc gctagtaatc gtagatcaga tatgctacgg    1320
tgaatacgtt cccgggtctt gtactcaccg cccgtcacac catgggagtt gaattcaccc    1380
gaagccggaa tactaaatta gttaccgacc acggtgggtt cagcgactgg gg            1432
```